US00PP14641P29

(12) United States Plant Patent
Denis

(10) Patent No.: US PP14,641 P2
(45) Date of Patent: Mar. 30, 2004

(54) CTENANTHE PLANT NAMED 'AMAGRIS'

(50) Latin Name: *Ctenanthe oppenheimiana*
Varietal Denomination: Amagris

(75) Inventor: René Denis, Destelbergen (BE)

(73) Assignee: Denis-Plants BVBA, Lochristi (BE)

( * ) Notice: Subject to any disclaimer, the term of this patent is extended or adjusted under 35 U.S.C. 154(b) by 0 days.

(21) Appl. No.: 10/358,976

(22) Filed: Feb. 5, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Ctenanthe plant named 'Amagris', characterized by its compact plant habit; narrow leaf shape; upper leaf surface grayed green in color with dark green margins and venation; and lower leaf surface grayed purple in color.

1 Drawing Sheet

Botanical classification/cultivar designation: *Ctenanthe oppenheimiana* cultivar Amagris.

BACKGROUND OF THE INVENTION

The present Invention relates to a new and distinct cultivar of Ctenanthe plant, botanically known as *Ctenanthe oppenheimiana*, and hereinafter referred to by the cultivar name Amagris.

The new Ctenanthe is a naturally-occurring whole plant mutation of *Ctenanthe oppenheimiana* selection known as burle-marxii, not patented. The new Ctenanthe was discovered and selected by the Inventor as a plant within a population of plants of the parent selection in a controlled environment in Beervelde-Lochristi, Belgium in June, 2000.

Asexual reproduction of the new cultivar by tissue culture micropropagation at Beervelde-Lochristi, Belgium since 2000, has shown that the unique features of this new Ctenanthe are stable and reproduced true to type in successive generations.

SUMMARY OF THE INVENTION

The following traits have been repeatedly observed and are determined to be the unique characteristics of 'Amagris'. These characteristics in combination distinguish 'Amagris' as a new and distinct Ctenanthe cultivar:

1. Compact plant habit.
2. Narrow leaf shape.
3. Upper leaf surface grayed green in color with dark green margins and venation.
4. Lower leaf surface grayed purple in color.

Plants of the new Ctenanthe are most similar to plants of the parent selection. In side-by-side comparisons conducted in Beervelde-Lochristi, Belgium, plants of the new Ctenanthe differed from plants of the parent cultivar in the following characteristics:

1. Plants of the new Ctenanthe were smaller than plants of the parent selection.
2. Plants of the new Ctenanthe were fuller than plants of the parent selection.
3. Plants of the new Ctenanthe had a slower growth rate than plants of the parent selection.

4. Plants of the new Ctenanthe had narrower and shorter leaves than plants of the parent selection.
5. Plants of the new Ctenanthe and the parent selection differed in leaf color as plants of the new Ctenanthe had grayed green-colored upper leaf surfaces whereas plants of the parent selection had green-colored upper leaf surfaces.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new Ctenanthe. The photograph comprises a top perspective view of a typical plant of 'Amagris'.

DETAILED BOTANICAL DESCRIPTION

The cultivar Amagris has not been observed under all possible environmental conditions. The phenotype may vary somewhat with variations in environment such as temperature and light intensity, without, however, any variance in genotype. The aforementioned photograph and the following observations and measurements describe plants grown in Lochristi, Belgium under commercial practice in a glass-covered greenhouse with day and night temperatures about 20 to 21° C. Plants used in the photograph and following description were about 27 weeks old from a rooted micropropagated plant and grown in 12-cm containers. In the following description, color references are made to The Royal Horticultural Society Colour Chart, 2001 Edition, except where general terms of ordinary dictionary significance are used.

Botanical classification: *Ctenanthe oppenheimiana* Burle-marxii cultivar Amagris.

Parentage: Naturally-occurring whole plant mutation of *Ctenanthe oppenheimiana* selection known as burle-marxii, not patented.

Propagation:

*Type.*—By tissue culture.

*Time to initiate roots on a micropropagated plantlet.*—About 21 days at 20 to 21° C.

*Time to produce a rooted micropropagated plant.*—About 14 to 16 weeks at 20 to 21° C.

*Root description.*—Fine, freely branching and dense; creamy white in color.

Plant description:

*General appearance.*—Basal rosette of leaves; leaves, long-petioled; upright flowers on racemes. Overall flattened globular plant shape; compact; broadly spreading plant form.

*Growth habit.*—Leaves developing at the base; full and dense growth habit.

*Plant height.*—About 17 cm.

*Plant diameter.*—About 28 cm.

*Foliage description.*—Arrangement: Basal; alternate; simple; long-petioled. Length: About 9.6 cm. Width: About 4.6 cm. Shape: Oval-obovate to oblong. Apex: Abruptly acute. Base: Acute. Margin: Entire. Texture, upper and lower surfaces: Smooth, glabrous; somewhat leathery. Venation pattern: Pinnate. Color: Developing leaves, upper surface: 191A; towards the margin, between 139A and N189A. Developing leaves, lower surface: N186C. Fully expanded leaves, upper surface: 191A to 138B; towards the margin, between 139A and N189A. Fully expanded leaves, lower surface: N186C. Venation, upper surface: Primary or midvein vein, 143A; secondary or lateral veins, between 139A and N189A. Venation, lower surface: Primary or midvein vein, N186C; secondary or lateral veins, N186A to N186B. Petioles: Length, including geniculum: About 9.2 cm. Diameter: Proximal, about 4 mm; distal, just below geniculum, about 2.5 mm. Texture: Smooth. Color, developing leaves: 143B to 143C. Color, fully expanded leaves: 147A; towards the base, 197A. Geniculum: Length: About 9 mm. Diameter: About 2 mm. Texture: Upper surface, sparsely pubescent; lower surface, glabrous. Color, upper and lower surfaces: 147A to 147B. Petiole wings: Quantity per petiole: Two. Length: About 6.8 cm. Width: About 4 mm. Texture: Smooth. Color: Upper surface, 146C to 146D; lower surface, 147C.

Flower description:

*Flower type and flowering habit.*—Zygomorphic flowers arranged on basal racemes; about 75 flowers on the main raceme. Flowers not persistent. Flowers not fragrant. Flowers face outwardly.

*Flowering season.*—Plants typically flower during the summer, July to September, in Lochristi, Belgium; flowering continuously during this period.

*Inflorescence length.*—About 52 cm.

*Inflorescence diameter.*—About 16 cm.

*Flower diameter.*—About 5.7 cm.

*Flower depth.*—About 3.8 cm.

*Flower buds.*—Length: About 3.2 cm. Diameter: About 9 mm. Shape: Obovate. Color: Upper surface, 22B; lower surface, 145C; towards the apex, 143A to 143B.

*Petals.*—Quantity per flower: About three or four. Length: About 2.6 cm. Width: About 1.4 cm. Shape: Obovate to oblanceolate. Apex: Obtuse. Margin: Entire. Texture: Smooth, glabrous; towards margins, sparsely pubescent. Color: When developing, upper surface: 38B; towards center and base, 145B to 145D. When developing, lower surface: 38B; towards center and base, 145A to 145C. Fully developed, upper surface: 51B to 51C; towards center and base, 145D. Fully developed, lower surface: 51B; towards center and base, 145B to 145C.

*Petaloids.*—Quantity per flower: About 22. Length: About 2.4 cm. Width: About 1.3 cm. Shape: Outer petaloids, obovate to oblanceolate; inner petaloids, oblanceolate to narrowly oblanceolate. Apex: Obtuse. Margin: Entire. Texture: Smooth, glabrous; towards margins, sparsely pubescent. Color: When developing, upper surface: 38B; towards center and base, 145B to 145D. When developing, lower surface: 38B; towards center and base, 145A to 145C. Fully developed, upper surface: 51B to 51C; towards center and base, 145D. Fully developed, lower surface: 51B; towards center and base 145B to 145C.

*Sepals.*—Arrangement: Sepals rotate, slightly cup-shaped. Quantity per flower: About five. Length, upper sepal: About 2.3 cm. Length, lateral and lower sepals: About 2.5 cm. Width, upper and two lower sepals: About 1.4 cm. Width, lateral sepals: About 1.7 cm. Shape, all sepals: Obovate to elliptic. Apex, uppermost sepal: Acute. Apex, lateral and lower sepals: Obtuse. Base, upper sepal: Ending in a spur, about 2 cm in length. Base, lateral and lower sepals: Cuneate. Margin, all sepals: Entire. Texture, all sepals: Smooth, glabrous. Color, all sepals: When developing, upper surface: 38B; spot at apex, 144B to 144C. When developing, lower surface: 38B; spot at apex, 143A to 143C. Fully developed, upper surface: 51B to 51C; towards base, 145C. Fully developed, lower surface: 51B to 51C; towards base, 143B.

*Flower bracts.*—Quantity per flower: One. Length: About 1.7 cm. Shape: Linear. Apex: Acute. Color: 143B.

*Peduncles.*—Length: About 46 cm. Diameter: About 5 cm. Angle: About 0 to 10° from vertical. Strength: Strong. Texture: Smooth, glabrous. Color: 143A to 143B.

*Pedicels.*—Length: About 9.6 cm. Diameter: About 1.5 mm. Angle: About 5 to 25° from vertical. Strength: Strong. Texture: Smooth, glabrous. Color: 143A to 143B.

*Reproductive organs.*—Androecium: Quantity of stamens per flower: About four. Stamen length: About 2 mm. Anther shape: Oblong. Anther color: 200C. Amount of pollen: Scarce. Pollen color: 157B. Gynoecium: Quantity of pistils per flower: About five. Pistil length: About 9 mm. Stigma shape: Two-parted. Stigma color: Close to N155C. Style length: About 7.5 mm. Style color: 186A to 186B. Ovary color: 152C to 152D.

*Seed/fruit.*—Seed and fruit development has not been observed.

Disease/pest resistance: Plants of the new Ctenanthe have not been observed to be resistant to pathogens and pests common to Ctenanthe.

Temperature tolerance: Plants of the new Ctenanthe have been observed to tolerate temperatures from 5 to 30° C.

It is claimed:

1. A new and distinct cultivar of Ctenanthe plant named 'Amagris', as illustrated and described.

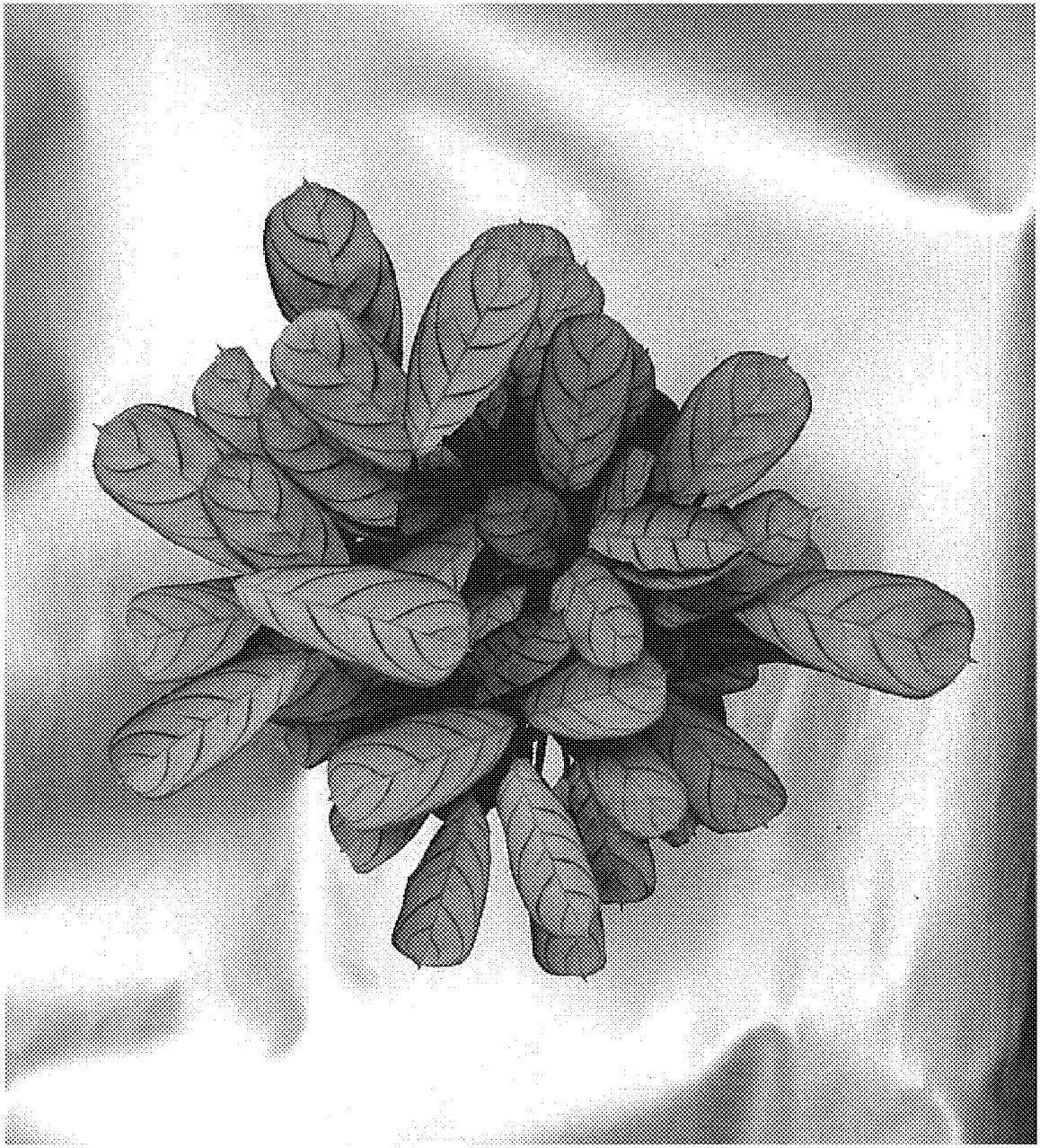

* * * * *